(12) United States Patent
Liu et al.

(10) Patent No.: US 9,955,924 B2
(45) Date of Patent: May 1, 2018

(54) MAGNETIC NANOPARTICLE TEMPERATURE IMAGING METHOD AND MAGNETIC NANOPARTICLE TEMPERATURE IMAGING SYSTEM

(71) Applicant: HUAZHONG UNIVERSITY OF SCIENCE AND TECHNOLOGY, Wuhan (CN)

(72) Inventors: Wenzhong Liu, Wuhan (CN); Shiqiang Pi, Wuhan (CN); Wenping Mao, Wuhan (CN); Jing Zhong, Wuhan (CN); Le He, Wuhan (CN)

(73) Assignee: HUAZHONG UNIVERSITY OF SCIENCE AND TECHNOLOGY, Wuhan (CN)

( * ) Notice: Subject to any disclaimer, the term of this patent is extended or adjusted under 35 U.S.C. 154(b) by 172 days.

(21) Appl. No.: 14/431,777

(22) PCT Filed: Apr. 14, 2014

(86) PCT No.: PCT/CN2014/075302
§ 371 (c)(1),
(2) Date: Mar. 27, 2015

(87) PCT Pub. No.: WO2015/149388
PCT Pub. Date: Oct. 8, 2015

(65) Prior Publication Data
US 2016/0296175 A1    Oct. 13, 2016

(30) Foreign Application Priority Data
Apr. 1, 2014 (CN) .......................... 2014 1 0128659

(51) Int. Cl.
*A61B 5/01*      (2006.01)
*A61B 5/00*      (2006.01)
(Continued)

(52) U.S. Cl.
CPC .............. *A61B 5/7278* (2013.01); *A61B 5/01* (2013.01); *A61B 5/0515* (2013.01); *G01K 7/36* (2013.01); *G01R 33/1276* (2013.01)

(58) Field of Classification Search
CPC ......... A61B 5/05; A61B 5/0515; A61B 5/055; A61B 5/7278; A61B 5/01; A61L 31/18;
(Continued)

(56) References Cited

U.S. PATENT DOCUMENTS

| | | | |
|---|---|---|---|
| 8,498,837 B2 * | 7/2013 | Liu ........................ | G01K 7/36 702/130 |
| 9,301,693 B2 * | 4/2016 | Liu ........................ | A61B 5/01 |
| 9,534,963 B2 * | 1/2017 | Liu ........................ | A61B 5/01 |

\* cited by examiner

*Primary Examiner* — Elmer Chao

(57) ABSTRACT

The present disclosure relates to methods and systems for magnetic nanoparticle temperature imaging. Particularly, the present methods involve applying different combinations of magnetic fields to magnetic nanoparticles placed in a one-dimensional space, collecting AC magnetization signals of the magnetic nanoparticles, and analyzing the collected signals to obtain in vivo temperature information of the one-dimensional space. Different exciting magnetic fields are applied to the magnetic nanoparticles, so that one-dimensional temperature imaging is transformed into single-point temperature measurement of each minizone, and one-dimensional temperature imaging can be precisely and quickly achieved without knowing the concentration distribution of the magnetic nanoparticles.

10 Claims, 13 Drawing Sheets

(51) Int. Cl.
  *A61B 5/05* (2006.01)
  *G01K 7/36* (2006.01)
  *G01R 33/12* (2006.01)

(58) Field of Classification Search
  CPC .......... B82Y 25/00; B82Y 15/00; A61F 2/82; G01R 33/5601; G01R 33/4808; G01R 33/1276; H01F 1/0045; G01K 7/36
  See application file for complete search history.

MAGNETIC NANOPARTICLE TEMPERATURE IMAGING METHOD AND MAGNETIC NANOPARTICLE TEMPERATURE IMAGING SYSTEM

CROSS REFERENCE TO RELATED APPLICATIONS

The present application is the US national stage of International Application PCT/CN2014/075302 filed on Apr. 14, 2014 which, in turn, claims priority to Chinese Patent Application CN2014101286595 filed on Apr. 1, 2014.

FIELD OF THE INVENTION

The invention relates to the field of nano measurement technology, and more particularly to a method for one-dimensional in-vivo temperature imaging based on paramagnetic property of magnetic nanoparticles.

BACKGROUND OF THE INVENTION

In-vivo temperature imaging refers to temperature imaging of tissues of a complete and survival individual. In the biomedical field such as hyperthermia cancer therapy, as it is so difficult to obtain temperature field distribution information in vivo accurately that many medical treatments cannot be used effectively. At present, in-vivo temperature measurement is categorized as invasive measurement and non-invasive measurement. Invasive measurement is simple and is able to monitor temperature of a lesion directly with high accuracy in real time. However, it is highly traumatic, the probe insertion tends to cause transfer of infected cells, the radiation of a heating source have affect on the probe directly may leading to decrease of measuring accuracy, and the measured temperature data is a point temperature which cannot construct temperature field distribution of the whole lesion. Meanwhile, non-invasive measurement can avoid wound infection or proliferation of cancer cells effectively and realize real-time imaging of an in-vivo temperature field with comparatively high accuracy, which enables it to have widely potential applications in the biomedical field.

Non-invasive measurement mainly includes infrared temperature measurement, ultrasonic temperature measurement, NMR temperature measurement and magnetic nanoparticle remote temperature measurement. Infrared temperature measurement measures temperature of a measured object according to infrared radiation intensity thereof, which is applicable for surface temperature measurement of objects instead of temperature field measurement deeply in tissues, and is vulnerable to emissivity of an object and aerosol particles. The key of ultrasonic temperature measurement is to measure propagation time of an ultrasonic accurately, which requires to measure acoustic characteristics and temperature characteristics of tissues in advance. However, temperature characteristics of tissues are instable and differ greatly therebetween, which affects temperature measurement significantly. NMR temperature measurement features high price and limited space resolution and temperature resolution, and is unfavorable for widespread applications. Non-invasive temperature field imaging by magnetic nanoparticles may overcome the above shortcomings, by which in-vivo temperature imaging may be realized thereby monitoring a hyperthermia cancer therapy process in real-time so as to make adjustments timely and effectively.

However, current non-invasive in-vivo temperature measurement method based on magnetic nanoparticles can only realize single-point temperature measurement instead of obtaining temperature field distribution deeply in tissues. Besides, accuracy of temperature measurement is affected by concentration distribution of magnetic nanoparticles deeply in tissues. Therefore, it is an urgent problem to be resolved in the field of magnetic nanoparticle hyperthermia cancer therapy that developing a method capable of realizing in-vivo temperature field imaging without knowing concentration distribution of magnetic nanoparticles.

SUMMARY OF THE INVENTION

In view of the above-mentioned problems, it is an objective of the invention to provide a method for in-vivo temperature imaging based on paramagnetic property of magnetic nanoparticles, so as to detect a one-dimensional in-vivo temperature field accurately without knowing concentration distribution of magnetic nanoparticles.

To achieve the above objective, in accordance with one embodiment of the present invention, there is provided a method for in-vivo temperature imaging by using magnetic nanoparticle, comprising steps of:

(1) positioning magnetic tracer agents at a one-dimensional space of interest;

(2) applying a DC magnetic field $H_{dc}=b$ and an AC excited magnetic field simultaneously to the one-dimensional space where the magnetic tracer agents are positioned, and collecting the AC magnetization signal of the magnetic tracer agents positioned at the one-dimensional space thereby obtaining amplitudes $A_1$, $A_3 \ldots A_{2j-1}$ of odd harmonics thereof, where the number of the harmonics $j \geq 2$, and b is the amplitude of the DC magnetic field;

(3) substituting a combined DC magnetic field $$H'_{dc} = \begin{cases} b & x < x_1 \\ f(x) & x_1 \leq x \leq x_1 + \Delta x \\ -b & x > x_1 + \Delta x \end{cases}$$

for the DC magnetic field in step (2) while keeping the AC excited magnetic field in step (2) unchanged, where x represents position, $x_1$ is the starting position of a DC gradient magnetic field $f(x)$ in the one-dimensional space, and $\Delta x$ is the width of the DC gradient magnetic field $f(x)$, and collecting the AC magnetization signal of the magnetic tracer agents again thereby obtaining amplitudes $B_1, B_3 \ldots B_{2j-1}$ of odd harmonics thereof;

(4) calculating variations $S_1, S_3 \ldots S_{2j-1}$ between amplitudes $B_1, B_3 \ldots B_{2j-1}$ of the odd harmonics in step (3) and those $A_1, A_3 \ldots A_{2j-1}$ of the odd harmonics in step (2);

(5) calculating y of an area of $[x_1, x_1+\Delta x]$ according to equations between the amplitude variations of odd harmonics and vivo temperature $$S_1 = \sum_{k=1}^{m} c \cdot f_1(y, z(r_k)) - \sum_{k=1}^{m} c \cdot f_1(y, z) \Big|_{z=b}$$

$$S_3 = \sum_{k=1}^{m} c \cdot f_3(y, z(r_k)) - \sum_{k=1}^{m} c \cdot f_3(y, z) \Big|_{z=b}$$

$$\vdots$$

-continued $$S_{2j-1} = \sum_{k=1}^{m} c \cdot f_{2j-1}(y, z(r_k)) - \sum_{k=1}^{m} c \cdot f_{2j-1}(y, z)\bigg|_{z=b}$$

thereby obtaining in-vivo temperature $$T = \frac{M_s}{k_0 \cdot y}$$

of the area of $[x_1, x_1+\Delta x]$, where $c=NM_S$, N is concentration of the magnetic nanoparticles, $M_s$ is effective atomic magnetic moment of the magnetic tarcer agent, $k_0$ is the Boltzmann's constant, the magnetization of the magnetic nanoparticles is described by the Langevin's function, $c \cdot f_{2j-1}(y, z(r_k))$ is the amplitude of a $(2j-1)^{th}$ harmonic obtained by finite terms of Taylor series expansion of the Langevin's function, $z(r_k)$ is the intensity of the DC magnetic field at a $k^{th}$ discrete point $r_k$ in the area of $[x_1, x_1+\Delta x]$, and m is the number of discrete points in the area of $[x_1, x_1+\Delta x]$; and (6) changing the starting position of the DC gradient magnetic field f(x) so that the DC gradient magnetic field f(x) with the width of $\Delta x$ moves to a next area, repeating steps (3)~(5) thereby obtaining the in-vivo temperature of the next area until temperature measurement of the whole one-dimensional space is completed.

In a class of this embodiment, the starting position of the DC gradient magnetic field in the measured one-dimensional space is changed by moving a DC magnetic field generating device or by changing current of the exciting coil.

In a class of this embodiment, in steps (2) and (3), amplitudes of odd harmonics of the AC magnetization signal of the magnetic nanoparticles are detected by a digital phase-sensitive detection method or by a least squares system parameter identification method.

In accordance with another embodiment, there is provided a magnetic nanoparticle temperature imaging system, comprising:

a DC magnetic field generating device is operable for applying a DC magnetic field $H_{dc}=b$ to a one-dimensional space where the magnetic tracer agents are positioned, where b is the amplitude of the DC magnetic field;

a combined DC magnetic field generating device is operable for applying a combined DC magnetic field $$H'_{dc} = \begin{cases} b & x < x_1 \\ f(x) & x_1 \leq x \leq x_1 + \Delta x \\ -b & x > x_1 + \Delta x \end{cases}$$

to the one-dimensional space where the magnetic tracer agents are positioned, where x represents position, $x_1$ is the starting position of a DC gradient magnetic field f(x) in the one-dimensional space, and $\Delta x$ is the width of the DC gradient magnetic field f(x);

an AC excited magnetic field generating device is operable for applying an AC excited magnetic field to the one-dimensional space where the magnetic tracer agents are positioned;

a magnetization collecting device is operable for collecting the AC magnetization signals of the magnetic tracer agents positioned at the one-dimensional space; and a processor is operable for processing an AC magnetization signal collected by applying the DC magnetic field and the AC excited magnetic field simultaneously to the magnetic nanoparticles thereby obtaining amplitudes $A_1, A_3 \ldots A_{2j-1}$ of odd harmonics thereof, processing an AC magnetization signal collected by applying the combined DC magnetic field and the AC excited magnetic field simultaneously to the magnetic nanoparticles thereby obtaining amplitudes $B_1, B_3 \ldots B_{2j-1}$ of odd harmonics thereof, calculating the variations $S_1, S_3 \ldots S_{2j-1}$ between amplitudes $B_1, B_3 \ldots B_{2j-1}$ of the odd harmonics and amplitudes $A_1, A_3 \ldots A_{2j-1}$ of the odd harmonics, and calculating y of an area of $[x_1, x_1+\Delta x]$ according to equations between the amplitude variations of odd harmonics and vivo temperature $$S_1 = \sum_{k=1}^{m} c \cdot f_1(y, z(r_k)) - \sum_{k=1}^{m} c \cdot f_1(y, z)\bigg|_{z=b}$$

$$S_3 = \sum_{k=1}^{m} c \cdot f_3(y, z(r_k)) - \sum_{k=1}^{m} c \cdot f_3(y, z)\bigg|_{z=b}$$

$$\vdots$$

$$S_{2j-1} = \sum_{k=1}^{m} c \cdot f_{2j-1}(y, z(r_k)) - \sum_{k=1}^{m} c \cdot f_{2j-1}(y, z)\bigg|_{z=b}$$

thereby obtaining in-vivo temperature $$T = \frac{M_s}{k_0 \cdot y}$$

of the area of $[x_1, x_1+\Delta x]$, where $c=NM_S$, N is concentration of the magnetic nanoparticles, $M_s$ is effective atomic magnetic moment of the magnetic nanoparticle, $k_0$ is the Boltzmann's constant, the magnetization of the magnetic nanoparticles is described by the Langevin's function, $c \cdot f_{2j-1}(y, z(r_k))$ is the amplitude of a $(2j-1)^{th}$ harmonic obtained by finite terms of Taylor series expansion of the Langevin's function, $z(r_k)$ is the intensity of the DC magnetic field at a $k^{th}$ discrete point $r_k$ in the area of $[x_1, x_1+\Delta x]$, m is the number of discrete points in the area of $[x_1, x_1+\Delta x]$, and the number of the harmonics $j \geq 2$.

Advantages of the invention comprise:

According to the present invention, firstly, the DC magnetic field and the AC magnetic field are applied simultaneously to the area where magnetic nanoparticles are positioned, and the AC magnetization signal of the magnetic nanoparticles is collected thereby obtaining amplitudes of harmonics thereof. Secondly, the combined DC magnetic field and the AC magnetic field are applied simultaneously to the area where the magnetic nanoparticles are positioned, and the AC magnetization signal of the magnetic nanoparticles is collected thereby obtaining amplitudes of harmonics thereof. Thirdly, amplitude variations of odd harmonics are obtained by amplitudes of odd harmonics in the second round minus amplitudes of odd harmonics in the first round. Under the above two magnetic excitations, the amplitude variations of odd harmonics in the whole measured area contain only signals of magnetic nanoparticles in an area with a width of $\Delta x$, namely only being relevant to temperature and concentration of the magnetic nanoparticles in the area with the width of $\Delta x$. Therefore, it is the concentration distribution of magnetic nanoparticles in an area with a width of Δx instead of in the whole one-dimensional area which affects temperature measurement. As Δx is very small, the concentration of magnetic nanoparticles in an area with a width of Δx may be considered as a constant, and therefore a whole one-dimensional space can be divided into multiple small areas with a width of Δx by applying different excited magnetic fields to magnetic nanoparticles, so that temperature imaging of the one-dimensional space is transformed to single-point temperature measurement of each of the small areas. The present invention is able to obtain temperature field of a one-dimensional space accurately and rapidly without knowing concentration of magnetic nanoparticles, and is especially applicable for temperature imaging of thermal motion at bio-molecular level. Simulation experiments show that it has a measurement error less than 0.79 K under a noise environment with an SNR of 80 dB.

BRIEF DESCRIPTION OF THE ACCOMPANYING DRAWINGS

FIG. 7 illustrates simulation results using amplitudes of harmonics detected by the DSPD algorithm with an exciting frequency of 160 Hz, an SNR of 90 dB and a temperature range of 308K~318K, where

FIG. 8 illustrates simulation results using amplitudes of harmonics detected by the DSPD algorithm with an exciting frequency of 160 Hz, an SNR of 80 dB and a temperature range of 308K~318K, where

FIG. 9 illustrates simulation results using amplitudes of harmonics detected by the DSPD algorithm with an exciting frequency of 160 Hz, an SNR of 90 dB and a temperature range of 300K~310K, where

FIG. 10 illustrates simulation results using amplitudes of harmonics detected by the DSPD algorithm with an exciting frequency of 160 Hz, an SNR of 80 dB and a test temperature of 300K~310K, where

FIG. 11 illustrates simulation results using amplitudes of harmonics detected by the DSPD algorithm with an exciting frequency of 160 Hz, an SNR of 80 dB, a deviation of magnetic field of 2% and a temperature range of 300K~310K, where

FIG. 12 illustrates simulation results using amplitudes of harmonics detected by the DSPD algorithm with an exciting frequency of 160 Hz, an SNR of 80 dB, a concentration distribution deviation of magnetic nanoparticles of 10% and a test temperature range of 300K~310K, where

Figure 14A:
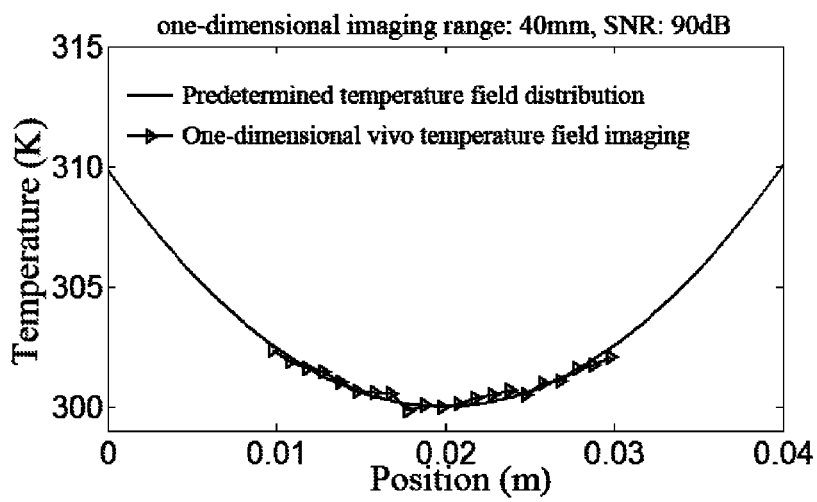
Figure 14B:
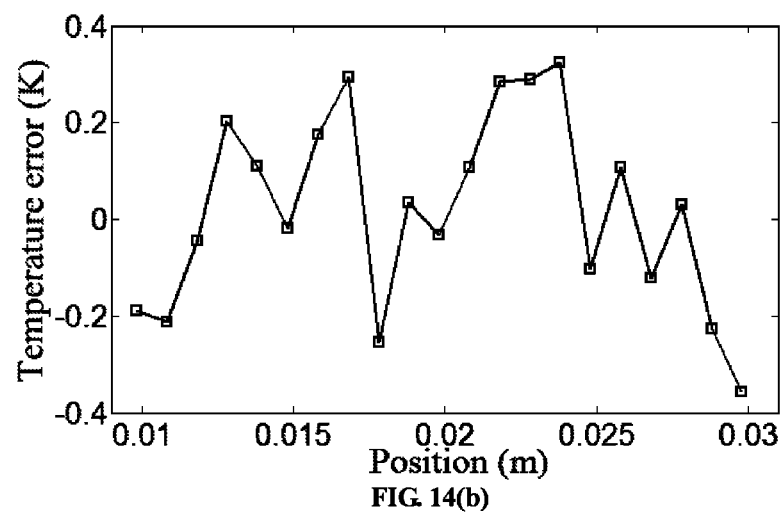
Figure 15A:
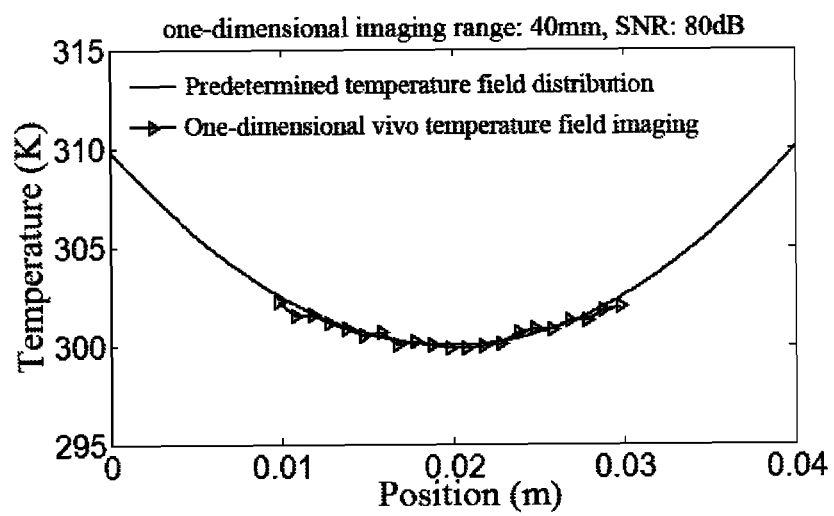
Figure 15B:
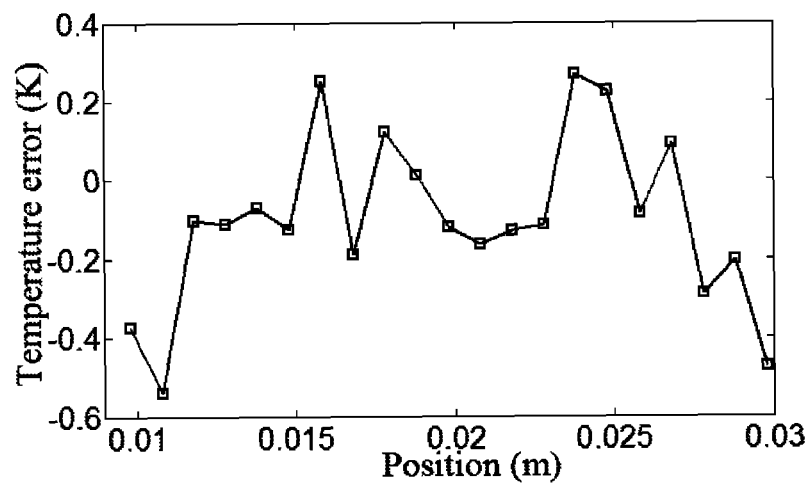

FIG. 14 illustrates simulation results using amplitudes of harmonics detected by the DSPD algorithm with an exciting frequency of 1.6 kHz, an SNR of 90 dB and a test temperature range of 300K~310K, where FIG. 14(a) illustrates a one-dimensional temperature imaging and FIG. 14(b) illustrates temperature imaging errors thereof; and FIG. 15 illustrates simulation results using amplitudes of harmonics detected by the DSPD algorithm with an exciting frequency of 1.6 kHz, an SNR of 80 dB and a test temperature range of 300K~310K, where FIG. 15(a) illustrates a one-dimensional temperature imaging and FIG. 15(b) illustrates temperature imaging errors thereof.

SPECIFIC EMBODIMENTS OF THE INVENTION

For clear understanding of the objectives, features and advantages of the invention, detailed description of the invention will be given below in conjunction with accompanying drawings and specific embodiments. It should be noted that the embodiments are only meant to explain the invention, and not to limit the scope of the invention.

Figure 1:
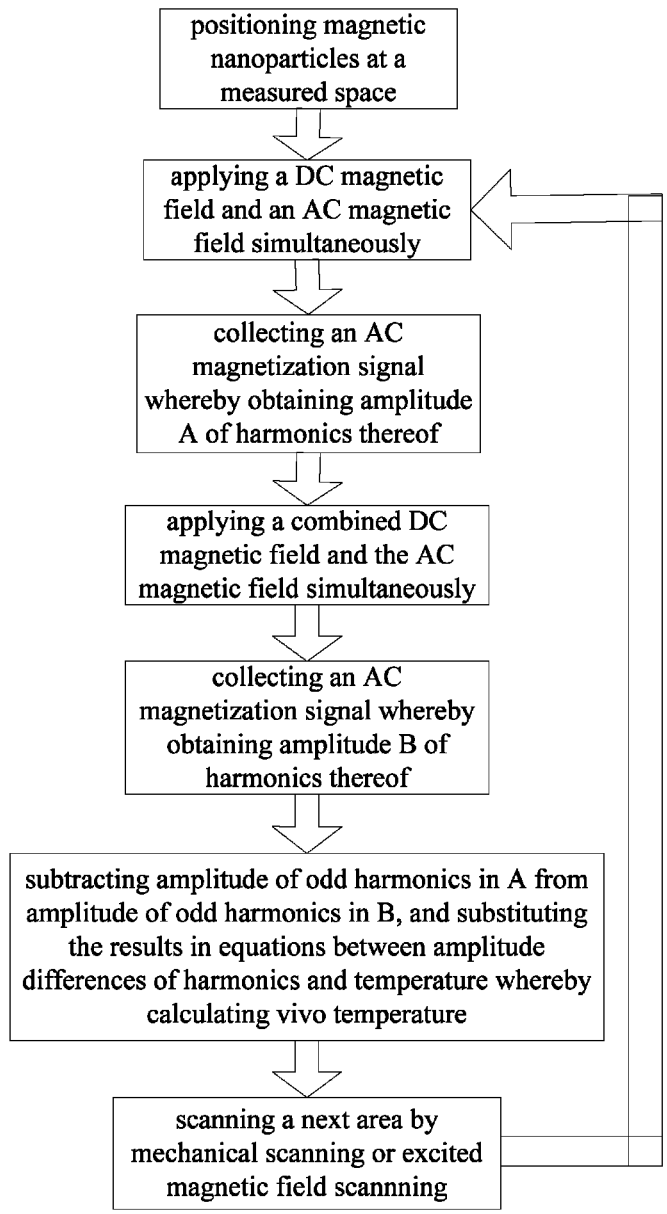
FIG. 1 is a flow chart of a method according to the present invention.
Figure 2:
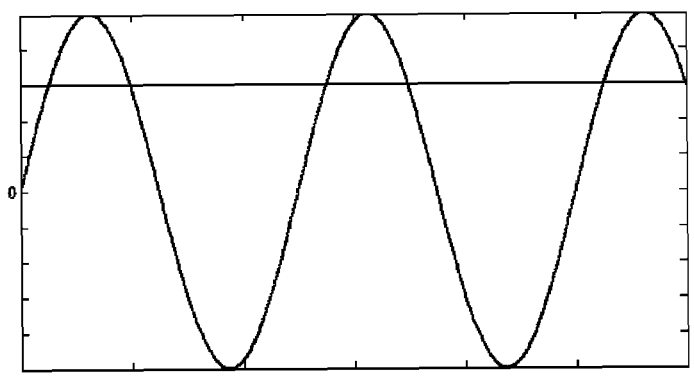
FIG. 2 illustrates a DC magnetic field and an AC excited magnetic field being applied simultaneously.

Referring to FIG. 1, a method for magnetic nanoparticle temperature imaging of the present invention comprises:

(1) positioning a magnetic tracer agents at a measured object;

injecting magnetic nanoparticles packaged with a surface bio-molecular modifier into a human body or an animal body to position them at a measured object (such as cancerous tissues of a human body or an animal body) by the blood circulatory system;

(2) collecting amplitudes of odd harmonics for the first time;

(21) applying a DC magnetic field $H_{dc}=b$ and an AC excited magnetic field $H(t)=H_0 \sin(2\pi ft)$ simultaneously to an area where the magnetic tracer agent is positioned, where a total magnetic field $H(t)=H_0 \sin(2\pi ft)+H_{dc}$, $H_0$ is the amplitude of the AC excited magnetic field, f is frequency thereof, and t represents time, as shown in FIG. 2;

As only finite terms of Taylor series expansion of the Langevin's function is used for in-vivo temperature calculation in following steps, considering truncation errors of the model, both amplitude of the AC excited magnetic field $H_0$ and that of the DC magnetic field b should be small. However, if an applied magnetic field were too weak, the background noise would become greater comparatively, which decreases the SNR and is unfavorable for signal extraction. Therefore, it is of great importance to choose the intensity of the AC excited magnetic field and that of the DC magnetic field reasonably, and amplitudes thereof may be adjusted according to experimental results.

Figure 3:
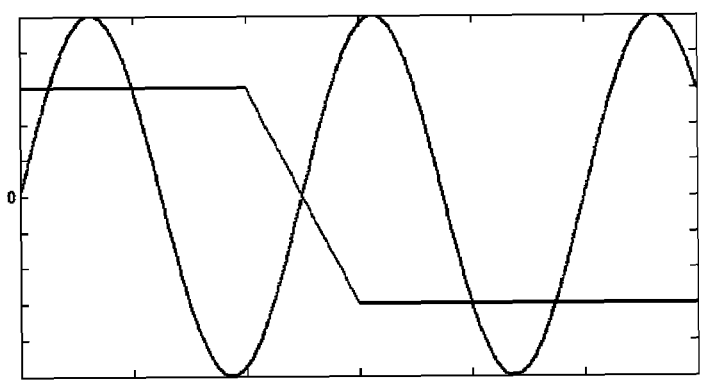
FIG. 3 illustrates a combined DC magnetic field and an AC excited magnetic field being applied simultaneously.

(22) collecting the AC magnetization signal of the magnetic tracer agents in the measured area;

detecting AC magnetization of the magnetic nanoparticles in the measured area using a solenoid or a small coil as a sensor, which is collected by a data acquisition card and is stored in a computer for following data processing after being processed by conditioning circuits such as an amplifier circuit;

(23) detecting amplitudes $A_1, A_3 \ldots A_{2j-1}$ of odd harmonics of the AC magnetization signal, where the number of the harmonics $j \geq 2$;
  detecting the amplitudes of harmonics of the AC magnetization signal collected by the data acquisition card by the digital phase-sensitive detection method (DPSD) or by the least squares system parameter identification method;
(3) collecting amplitudes of odd harmonics for the second time;
(31) removing the constant DC magnetic field, and applying a combined DC magnetic field $$H'_{dc} = \begin{cases} b & x < x_1 \\ f(x) & x_1 \leq x \leq x_1 + \Delta x \\ -b & x > x_1 + \Delta x \end{cases}$$

to the area where the magnetic tracer agents are positioned while keeping the AC excited magnetic field $H(t)=H_0 \sin(2\pi ft)$ unchanged, where x represents position, $x_1$ is the starting position of a DC gradient magnetic field f(x) in the one-dimensional space, and $\Delta x$ is the width of the DC gradient magnetic field f(x), a DC magnetic field z is a linear or nonlinear gradient magnetic field in an area of $\Delta x$, z=b and z=−b respectively on two sides of the gradient magnetic field, and a total magnetic field $H(t)=H_0 \sin(2\pi ft)+H_{dc}'$, as shown in FIG. 3;

It should be noted that the intensity of the magnetic field on two sides of the DC gradient magnetic field should equal that of the constant DC magnetic field in step (2), and the amplitude and frequency of the AC excited magnetic field should keep unchanged. Besides, too great magnetic field intensity b may lead to changes of positive-negative signs of odd harmonics of the magnetic nanoparticles under the gradient magnetic field, which brings errors to in-vivo temperature measurement.

(32) collecting an AC magnetization signal of the magnetic tracer agents in the measured area;
  consistent with step (22), detecting AC magnetization of the magnetic nanoparticles in the measured area using a solenoid or a small coil as a sensor, which is collected by a data acquisition card and is stored in a computer for following data processing after being processed by conditioning circuits such as an amplifier circuit;
(33) detecting amplitudes $B_1, B_3 \ldots B_{2j-1}$ of odd harmonics of the AC magnetization signal, where the number of the harmonics $j \geq 2$;
  consistent with step (23), detecting the amplitudes of harmonics of the AC magnetization signal collected by the data acquisition card by the digital phase-sensitive detection method (DPSD) or by the least squares system parameter identification method;
(4) calculating variations $S_1, S_3 \ldots S_{2j-1}$ between amplitudes $B_1, B_3 \ldots B_{2j-1}$ of the odd harmonics in step (3) and those $A_1, A_3 \ldots A_{2j-1}$ of the odd harmonics in step (2);
(5) calculating in-vivo temperature according to equations between the amplitude variations of odd harmonics and in-vivo temperature;

Magnetization of magnetic nanoparticles may be described by the Langevin's function as follows:

$$M = NM_s \left( \coth(\alpha) - \frac{1}{\alpha} \right)$$

where $$\alpha = \frac{M_s H}{k_0 T},$$

H is a magnetic field applied to the magnetic nanoparticles, N is concentration of the magnetic nanoparticles, $M_s$ is effective atomic magnetic moment of the magnetic nanoparticles, $k_0$ is the Boltzmann's constant, and T is absolute temperature of a measured object.

When $H(t)=H_0 \sin(2\pi ft)+z$, namely an AC magnetic field and a DC magnetic field are applied simultaneously to the magnetic nanoparticles, the amplitudes of harmonics may be derived approximately by finite terms of Taylor series expansion.

Amplitude of the first harmonic is as follows:

$$Amp_1 = c\left[\frac{1}{3}H_0 y - \left(\frac{1}{60}H_0^3 + \frac{1}{15}H_0 z^2\right)y^3 + \left(\frac{1}{756}H_0^5 + \frac{1}{63}H_0^3 z^2 + \frac{2}{189}H_0 z^4\right)y^5 + \ldots \right]$$

which is simplified as $Amp_1 = c \cdot f(y,z)$;
amplitude of the second harmonic is as follows:

$$Amp_2 = c\left[\frac{1}{30}H_0^2 z y^3 - \left(\frac{1}{189}H_0^4 z + \frac{2}{189}H_0^2 z^3\right)y^5 + \ldots \right]$$

which is simplified as $Amp_2 = c \cdot f(y,z)$;
amplitude of the third harmonic is as follows:

$$Amp_3 = c\left[\frac{1}{180}H_0^3 y^3 - \left(\frac{1}{1512}H_0^5 + \frac{1}{189}H_0^3 z^2\right)y^5 + \ldots \right]$$

which is simplified as $Amp_3 = c \cdot f_3(y,z)$; and
amplitude of the $n^{th}$ harmonic is simplified as $Amp_n = c \cdot f_n(y,z)$,
where $c = NM_s$, $$y = \frac{M_s}{k_0 T},$$

N is concentration of the magnetic nanoparticles, $M_s$ is effective atomic magnetic moment of the sample, $k_0$ is the Boltzmann's constant, T is absolute temperature of the measured object, z is intensity of the DC magnetic field, and $H_0$ is an amplitude of the AC magnetic field.

Figure 4:
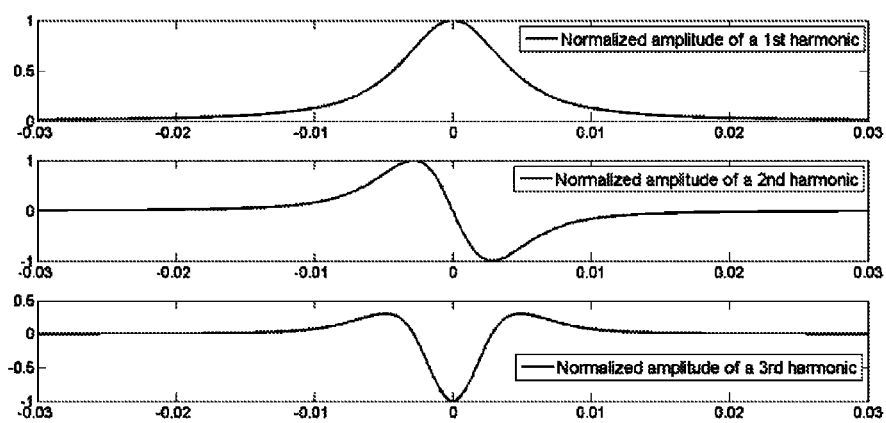
FIG. 4 illustrates a first harmonic, a second harmonic and a third harmonic changing with a DC magnetic field.

It can be derived by mathematical induction that odd harmonics are even functions with respect to the DC magnetic field z, and even harmonics are odd functions with respect to the DC magnetic field z, namely $f_{2j-1}(z)=f_{2j-1}(-z)$ and $f_{2j}(-z)=-f_{2j}(z)$, where $j \geq 1$. As shown in FIG. 4, it is clear that the first harmonic and the third harmonic are even functions with respect to the DC magnetic field z, and the second harmonic is an odd function with respect to the DC magnetic field z. Therefore, when the applied magnetic field is changed from $H(t)=H_0 \sin(2\pi ft)+H_{dc}$ to $H(t)=H_0 \sin(2\pi ft)+H_{dc}'$, absolute values and signs of odd harmonics of magnetic nanoparticles under the DC magnetic field where $z=\pm b$ keep unchanged, and even harmonics thereof feature unchanged absolute values and opposite signs. Only the amplitudes of odd harmonics of magnetic nanoparticles in an area of $\Delta x$, where the DC magnetic field is a linear or nonlinear gradient magnetic field, change.

Figure 5:
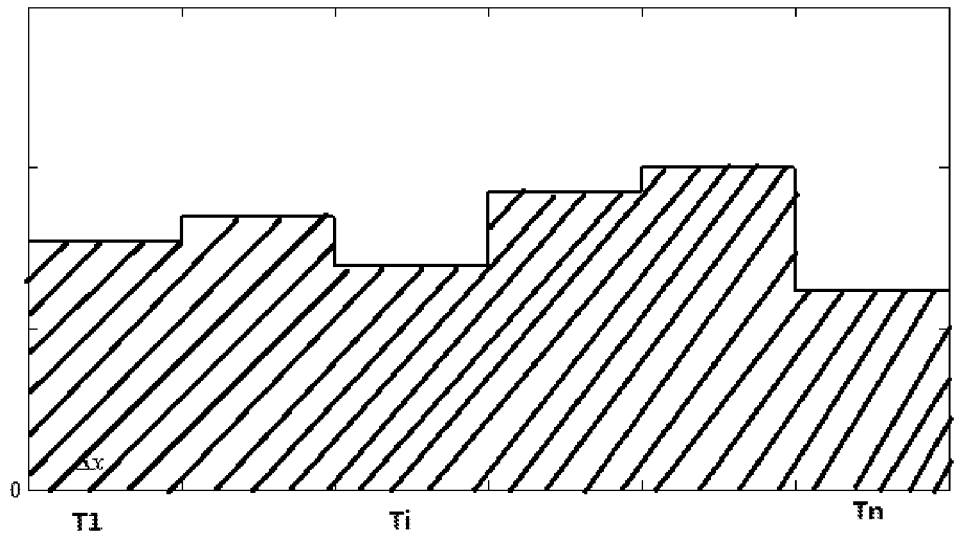
FIG. 5 illustrates amplitudes of first harmonics of magnetic nanoparticles in a measured area when a total magnetic field $H(t)=H_0 \sin(2\pi ft)+H_{dc}$ is applied.
Figure 6:
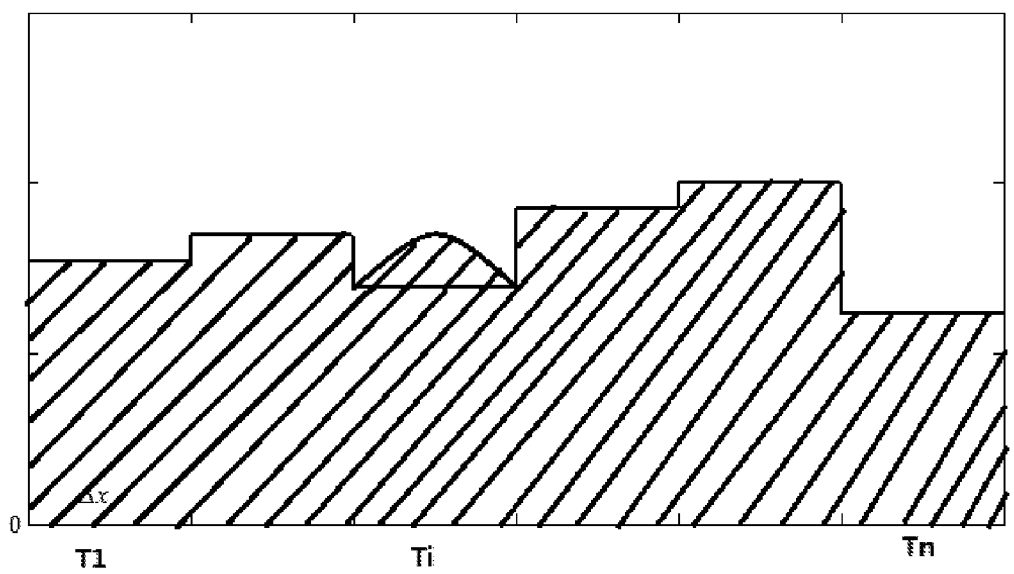
FIG. 6 illustrates amplitudes of first harmonics of magnetic nanoparticles in a measured area when a total magnetic field $H(t)=H_0 \sin(2\pi ft)+H_{dc}'$ is applied.
Figure 7A:
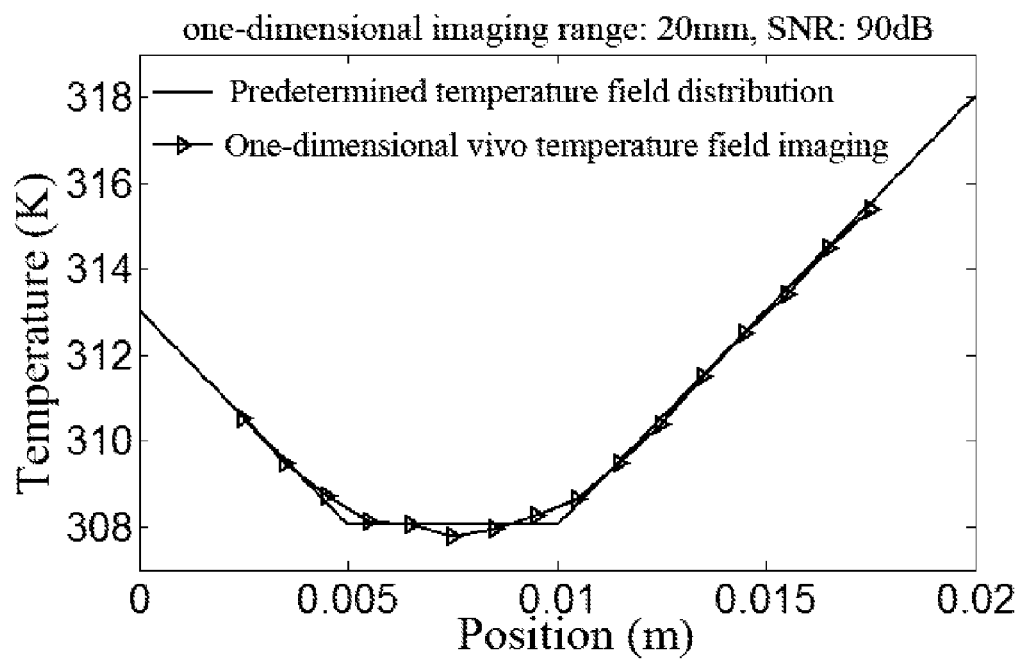
FIG. 7(a) illustrates a one-dimensional temperature imaging and FIG. 7(b) illustrates temperature imaging errors thereof.
Figure 7B:
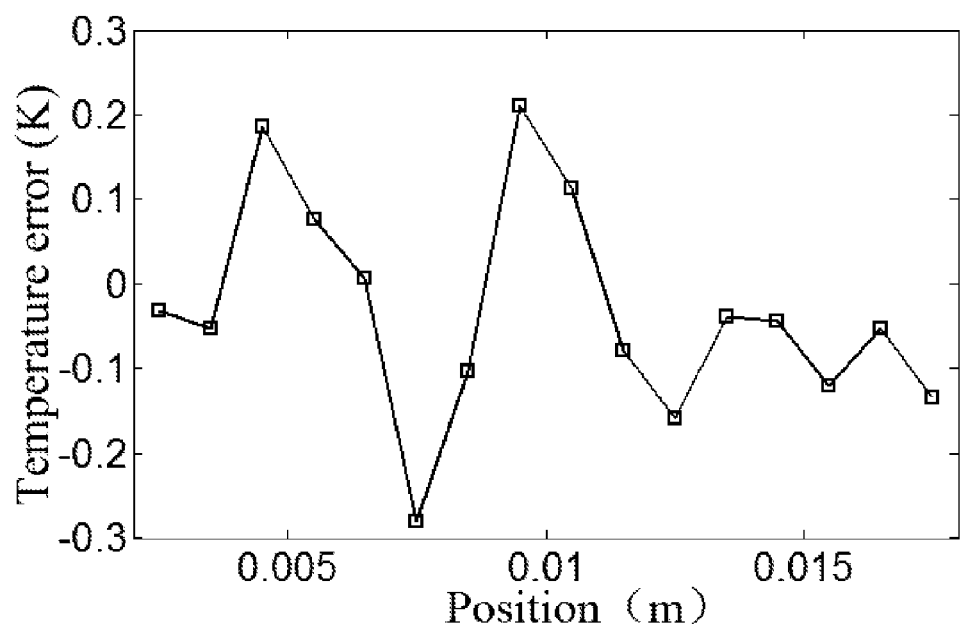
Figure 8A:
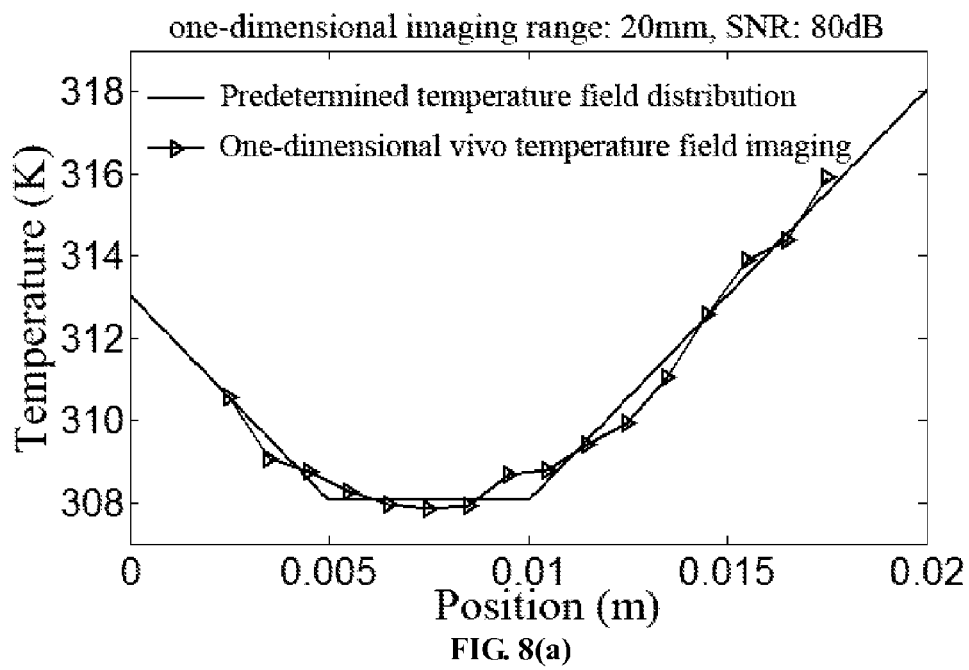
FIG. 8(a) illustrates a one-dimensional temperature imaging and FIG. 8(b) illustrates temperature imaging errors thereof.
Figure 8B:
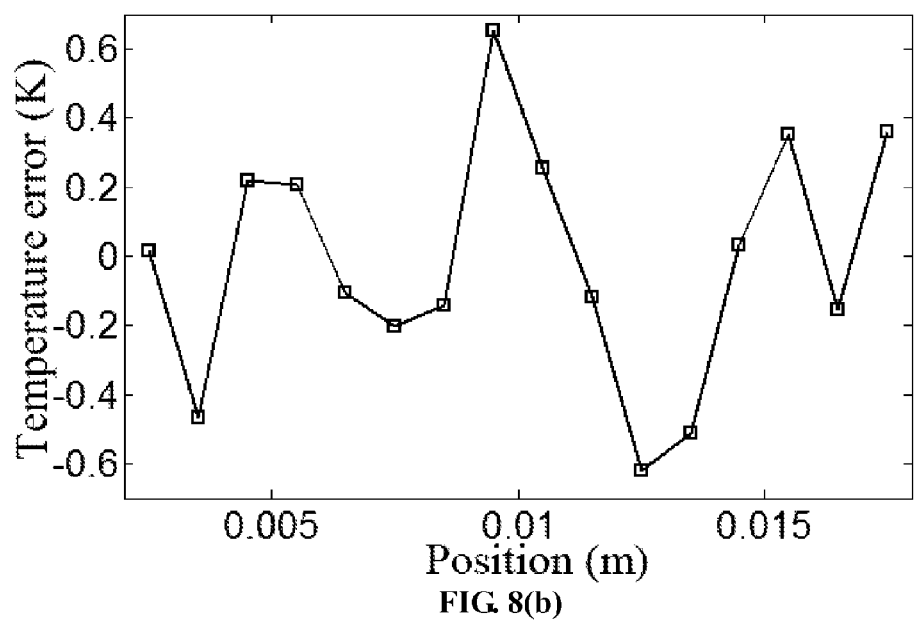
Figure 9A:
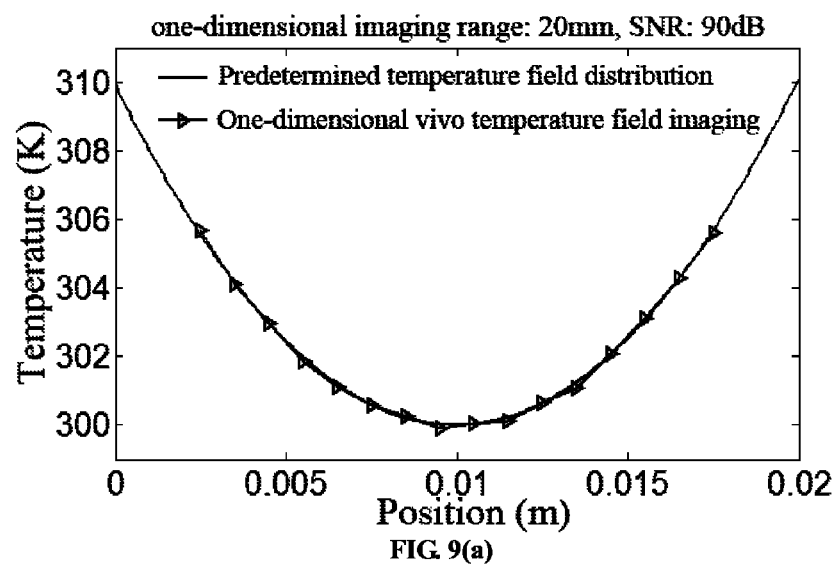
FIG. 9(a) illustrates a one-dimensional temperature imaging and FIG. 9(b) illustrates temperature imaging errors thereof.
Figure 9B:
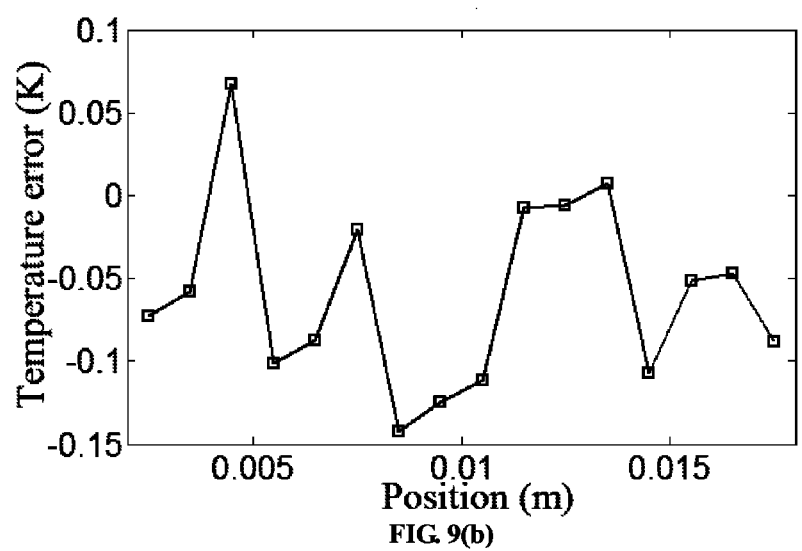
Figure 10A:
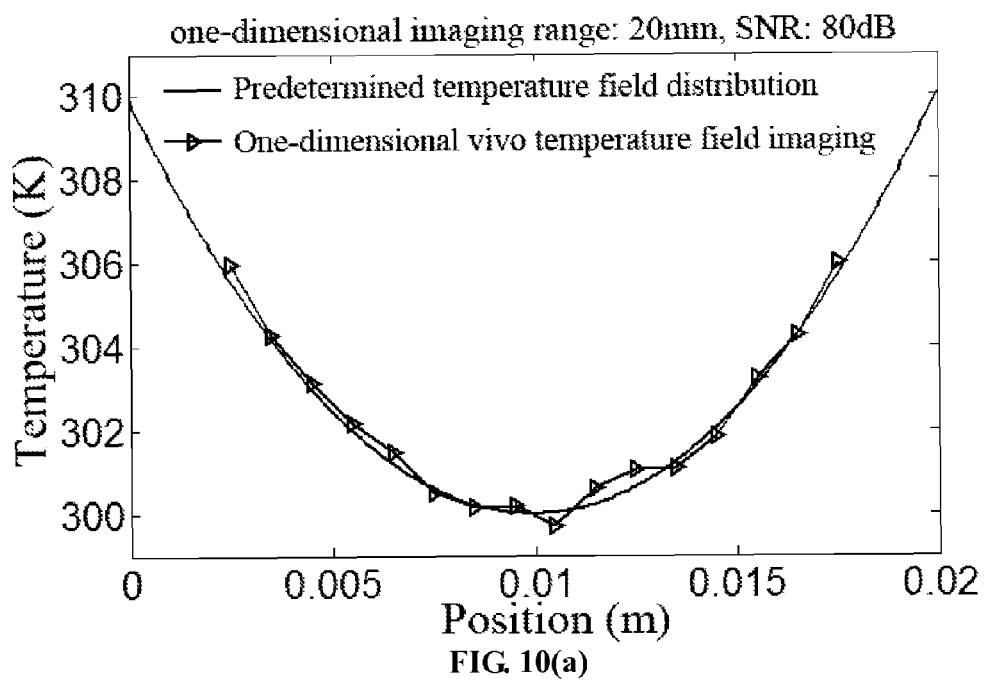
FIG. 10(a) illustrates a one-dimensional temperature imaging and FIG. 10(b) illustrates temperature imaging errors thereof.
Figure 10B:
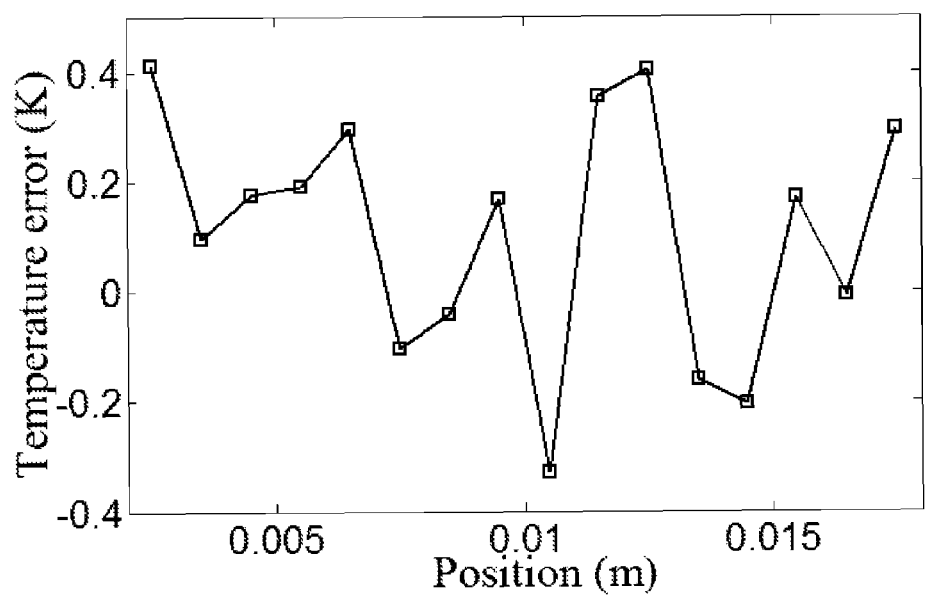

In order to further illustrate the present invention, amplitudes of harmonics changing with an applied excited magnetic field is analyzed in combination with FIG. 5 and FIG. 6, and equations between amplitude variations of odd harmonics and in-vivo temperature are derived. Since analyzing method of the first harmonic is the same as that of the other odd harmonics with higher order, only the first harmonic is analyzed in details in the present invention.

Regarding the measured area as temperature points $T_1$, $T_2 \ldots T_i \ldots T_n$, each of which takes an area with a width equal to that of the gradient magnetic field of the combined DC magnetic field $\Delta x$. As $\Delta x$ is very small, concentration of magnetic nanoparticles in an area of $\Delta x$ may be considered as a constant.

When a magnetic field $H(t)=H_0 \sin(2\pi ft)+H_{dc}$ is applied to the measured area, according to the Langevin's function, amplitude of a first harmonic of magnetic nanoparticles in an area of $\Delta x$ with a same temperature $T_i$ is constant, as shown in FIG. 5. Therefore, amplitude of a first harmonic of magnetic nanoparticles in the whole one-dimensional space is the sum of that of magnetic nanoparticles at the different temperature points, which is represented by $A_1$.

When a magnetic field $H(t)=H_0 \sin(2\pi ft)+H_{dc}'$ is applied to the measured area, and the gradient magnetic field with a width of $\Delta x$ is located at a temperature point $T_i$, as a first harmonic is an even function with respect to a DC magnetic field z, namely $f_1(z)=f_1(-z)$, absolute values and signs of first harmonics of magnetic nanoparticles under the DC magnetic field where $z=\pm b$ keep unchanged, and only the amplitude of a first harmonic of magnetic nanoparticles in an area where the DC magnetic field z is a linear or nonlinear gradient magnetic field change. Amplitudes of first harmonics of magnetic nanoparticles at the temperature points in this case are shown in FIG. 6. Therefore, amplitude of a first harmonic of magnetic nanoparticles in the whole one-dimensional space is the sum of $A_1$ and the amplitude variation of the first harmonic in the area of the gradient magnetic field, which is represented by $B_1$.

Under the above two kinds of magnetic fields, amplitude variation between first harmonics of the whole measured area may be represented by $S_{1,i}=B_1-A_1$. In combination with FIG. 5 and FIG. 6, it is clear that $S_{1,i}$ actually represents amplitude variation between first harmonics of magnetic nanoparticles in an area of $\Delta x$ where a $i^{th}$ temperature point is located under the above two magnetic fields, which contains only signals of magnetic nanoparticles in the area of $\Delta x$ where the $i^{th}$ temperature point is located, namely it is only related with the temperature and concentration of magnetic nanoparticles at the $i^{th}$ temperature point. Therefore, it may be derived that it is concentration distribution of magnetic nanoparticles in the area with a width of $\Delta x$ instead of in the whole one-dimensional area which affects temperature measurement. Besides, as $\Delta x$ is very small, concentration of magnetic nanoparticles in the area with a width of $\Delta x$ may be considered as a constant.

Based on the above analysis, amplitude variation between first harmonics in an area of $[x_1, x_1+\Delta x]$ may be represented by:

$$S_1 = \int_\Omega c \cdot f_1(y, z(r))dr - \int_\Omega c \cdot f_1(y, z)\bigg|_{z=b} dr$$

where $C=NM_s$, N is concentration of the magnetic nanoparticles, $M_s$ is effective atomic magnetic moment of the magnetic nano sample, and $c \cdot f_1(y,z(r))$ represents amplitude of a first harmonic at $r\epsilon\Omega$, where $\Omega=[x_1, x_1+\Delta x]$.

Similarly, amplitude variation between third harmonics in an area of $[x_1, x_1+\Delta x]$ may be represented by:

$$S_3 = \int_\Omega c \cdot f_3(y, z(r))dr - \int_\Omega c \cdot f_3(y, z)\bigg|_{z=b} dr$$

where $c \cdot f_3(y,z(r))$ represents amplitude of a third harmonic at $r\epsilon\Omega$, where $\Omega=[x_1, x_1+\Delta x]$.

Similarly, amplitude variation between $(2j-1)^{th}$ harmonics of the whole measured area may be represented by:

$$S_{2j-1} = \int_\Omega c \cdot f_{2j-1}(y, z(r))dr - \int_\Omega c \cdot f_{2j-1}(y, z)\bigg|_{z=b} dr$$

where $c \cdot f_{2j-1}(y,z(r))$ represents amplitude of a $(2j-1)^{th}$ harmonic at $r\epsilon\Omega$, where $\Omega=[x_1, x_1+\Delta x]$ and $j \geq 2$.

Overall, relationship between amplitude variations of odd harmonics of the magnetic nanoparticles and in-vivo temperature is established.

By discretizing the area of $\Omega$ where the $i^{th}$ temperature point is located into m segments, equations between amplitude variations of odd harmonics $S_{1,i} \ldots S_{2j-1,i}$ and in-vivo temperature are as follows:

$$S_{1,i} = \sum_{k=1}^{m} c_i \cdot f_1(y_i, z(r_k)) - \sum_{k=1}^{m} c_i \cdot f_1(y_i, z)\bigg|_{z=b}$$

$$S_{3,i} = \sum_{k=1}^{m} c_i \cdot f_3(y_i, z(r_k)) - \sum_{k=1}^{m} c_i \cdot f_3(y_i, z)\bigg|_{z=b}$$

$$\vdots$$

$$S_{2j-1,i} = \sum_{k=1}^{m} c_i \cdot f_{2j-1}(y_i, z(r_k)) - \sum_{k=1}^{m} c_i \cdot f_{2j-1}(y_i, z)\bigg|_{z=b}$$

$c_i$ and $y_i$ at the $i^{th}$ temperature point can be obtained by resolving the discrete equations thereby obtaining in-vivo temperature at the $i^{th}$ temperature point $$T_i = \frac{M_s}{k_0 \cdot y_i}$$

and its corresponding concentration of magnetic nanoparticles $$N_i = \frac{c_i}{M_s}.$$

When the number of detected odd harmonics $j=2$, $c_i$ and $y_i$ may be obtained by resolving the equations directly thereby obtaining in-vivo temperature at the $i^{th}$ temperature point $$T_i = \frac{M_s}{k_0 \cdot y_i}.$$

When the number of detected odd harmonics j≥3, $c_i$ and $y_i$ may be obtained by resolving overdetermined equations using algorithms such as the least square method thereby obtaining in-vivo temperature at the $i^{th}$ temperature point $$T_i = \frac{M_s}{k_0 \cdot y_i}.$$

(6) changing the starting position $x_1$ of the DC gradient magnetic field in the one-dimensional space by mechanical scanning or excited magnetic field scanning, so that the DC gradient magnetic field with the width of Δx moves to a next area, and recording a corresponding coordinate; and returning to step (2) if detection of the whole measured area is not completed, and ending the process if detection of the whole measured area is completed;

In mechanical scanning, the gradient magnetic field is enabled to scan the whole one-dimensional space by moving a magnetic field generating device via a motor or by moving the magnetic nanoparticles directly, and corresponding coordinates are recorded.

In excited magnetic field scanning, the gradient magnetic field is enabled to scan the whole one-dimensional space by methods such as changing current of an exciting coil, and corresponding coordinates are recorded.

When the scanning speed is high enough or the temperature changes slowly, $A_1$ detected in the first round is almost constant, and scanning of the whole imaging area may be completed by returning to step (3) directly instead of returning to step (2), where $A_1$ detected in the first round is subtracted from a signal obtained in each scanning, which may decrease temperature imaging time without affecting the accuracy of temperature measurement.

When distribution of magnetic nanoparticles in the one-dimensional space is comparatively uniform, amplitude differences of second harmonics may be used to locate coordinates of the temperature points. By drawing trend of amplitude differences of second harmonics, it may be inferred that the projection of the amplitude differences of the second harmonics of each temperature point onto the coordinate axis corresponds to its coordinate.

Simulation Example 1

1. Simulation Model and Test Explanation

In order to study the effectiveness and feasibility of the method for in-vivo temperature imaging, simulation data containing noise are used in the simulation to test the method. Effective magnetic moment $M_s$ of particles of a agent applied in the simulation is measured as $8.5 \times 10^{-19}$ (the effective magnetic moment is determined by the type of the tracer agents), and the width of the DC gradient magnetic field Δx=5 mm, which moves 1 mm each time by simulating mechanical movement. Considering truncation errors of an approximate model obtained by the first eight terms of Taylor series expansion of the Langevin's function, in the simulation, amplitude of the AC magnetic field $H_0$=50 Oe and frequency thereof is 160 Hz, the amplitude of the DC magnetic field is 30 Oe, and noise is added to AC magnetization signals by a awgn function in MATLAB. Following tests are conducted for different purposes:

(1) Concentration distribution of the magnetic nanoparticles is uniform, noise with an SNR of 90 dB or 80 dB is added in in-vivo temperature imaging of different temperature field distributions, test temperature is in a range of 308K~318K or 300K~310K, and simulation results are shown in FIG. 7~FIG. 10.

Figure 11A:
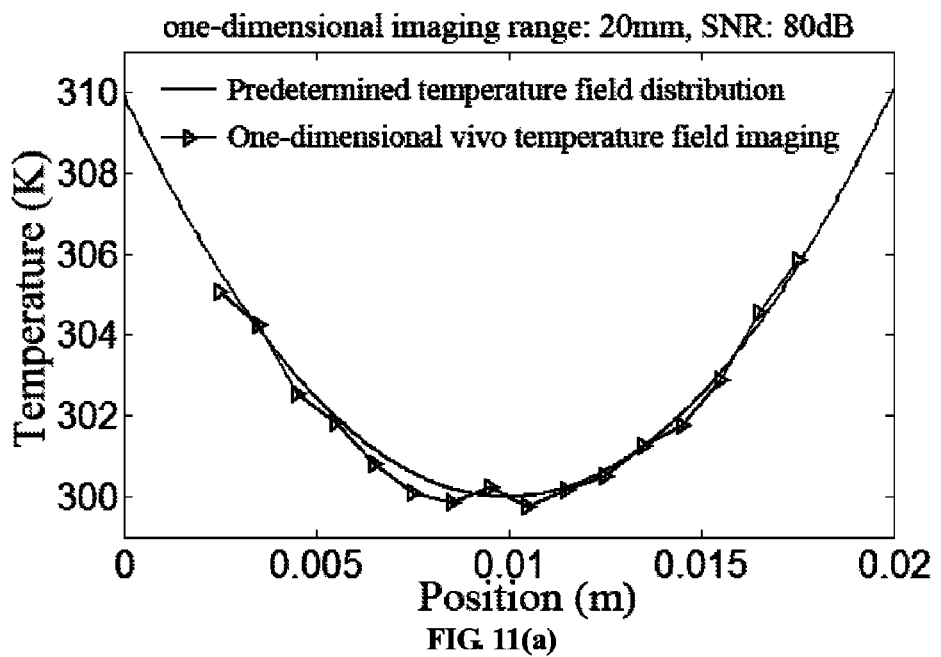
FIG. 11(a) illustrates a one-dimensional temperature imaging and FIG. 11(b) illustrates temperature imaging errors thereof.
Figure 11B:
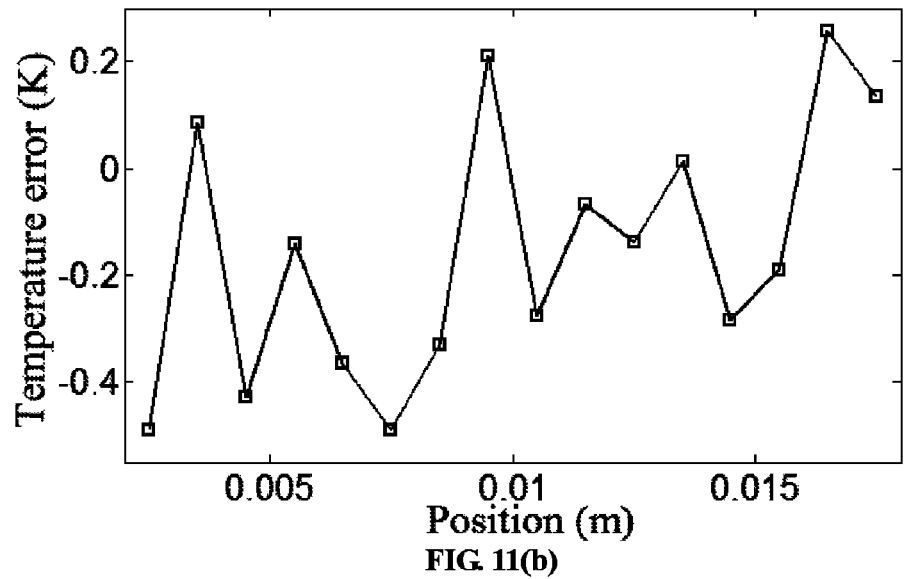

(2) Amplitude deviation of the DC magnetic field is 2%, noise with an SNR of 80 dB is added in temperature imaging, test temperature is in a range of 300K~310K, and simulation results are shown in FIG. 11.

Figure 12A:
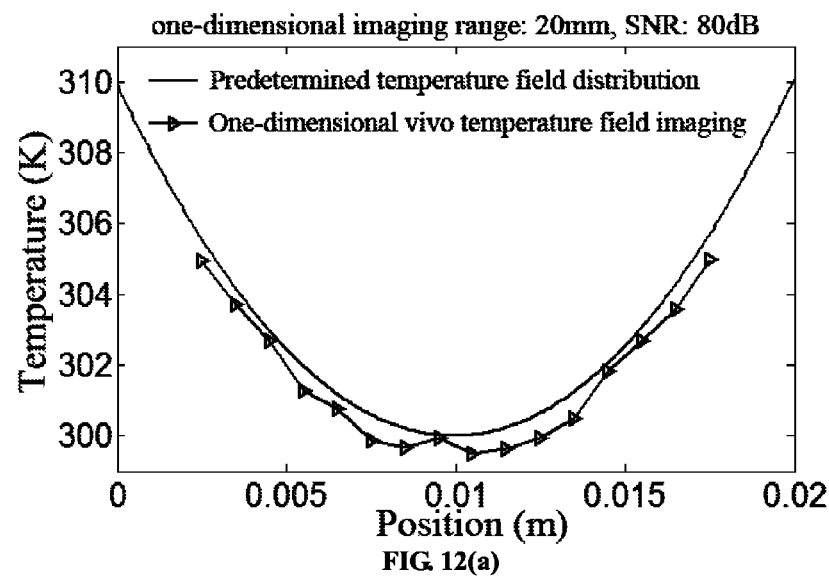
FIG. 12(a) illustrates a one-dimensional temperature imaging and FIG. 12(b) illustrates temperature imaging errors thereof.
Figure 12B:
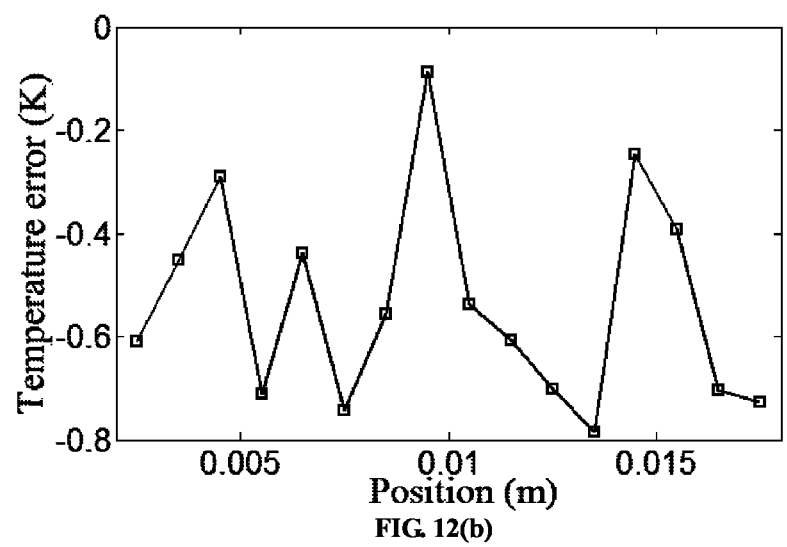
Figure 13:
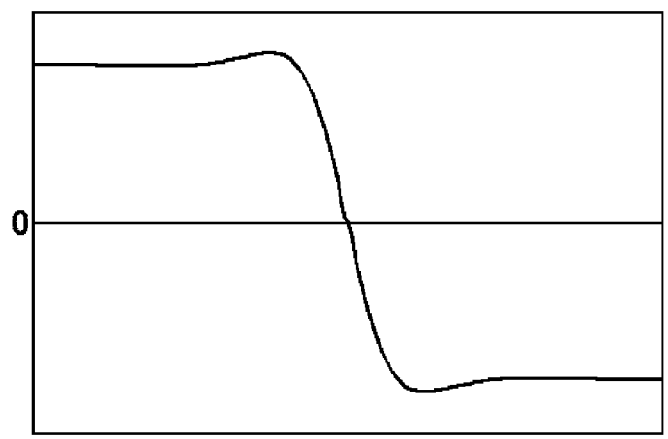
FIG. 13 illustrates a combined DC magnetic field containing a nonlinear DC gradient magnetic field.

(3) Concentration deviation of the magnetic nanoparticles is 10%, noise with an SNR of 80 dB is added in temperature imaging, test temperature is in a range of 300K~310K, and simulation results are shown in FIG. 12.

2. Simulation Results

FIG. 7~FIG. 10 show that temperature measurement error of the method for magnetic nanoparticle temperature imaging is less than 0.63K under different temperature field distributions. Since the test is carried out under SNRs of 80 dB and 90 dB respectively, the method has some anti-noise performance.

FIG. 11 illustrates accuracy and applicability of the method for one-dimensional in-vivo temperature imaging when deviation occurs in amplitude of the magnetic field. It can be inferred that temperature measurement error is less than 0.49K under an SNR of 80 dB, which shows that the method features comparatively high accuracy of temperature measurement when the amplitude of the magnetic field changes.

FIG. 12 illustrates accuracy and applicability of the method for one-dimensional in-vivo temperature imaging when concentration distribution of the magnetic nanoparticles is nonuniform. It can be inferred that temperature measurement error is less than 0.79K under an SNR of 80 dB, which shows that the method features comparatively high accuracy of temperature measurement in the case of unknown concentration and nonuniform concentration distribution.

Simulation Example 2

1. Simulation Model and Test Explanation

In order to study effectiveness of the method for magnetic nanoparticle temperature imaging when the DC gradient magnetic field is nonlinear, effective magnetic moment $M_s$ of particles of a agent applied in the simulation is measured as $8.5 \times 10^{-19}$ (the effective magnetic moment is determined by the type of the agents), the imaging range is 40 mm, the width of the DC gradient magnetic field Δx=20 mm, which moves 1 mm each time by simulating mechanical movement. A nonlinear DC gradient magnetic field is applied in the simulation. Amplitude of the AC magnetic field $H_0$=60 Oe and frequency thereof is 1.6 kHz, magnetization of the DC magnetic field is 30 Oe, and noise is added to AC magnetization signals by a awgn function in MATLAB. Concentration distribution of the magnetic nanoparticles is uniform, noise with an SNR of 90 dB or 80 dB is added in temperature imaging, test temperature is in a range of 300K~310K, and simulation results are shown in FIG. 14 and FIG. 15.

2. Simulation Results

FIG. 14 illustrates accuracy and applicability of the method for magnetic nanoparticle temperature imaging when the DC gradient magnetic field is nonlinear. It can be inferred that temperature measurement error is less than 0.36K under an SNR of 90 dB, which shows that the method features comparatively high accuracy of temperature measurement when the DC gradient magnetic field is nonlinear.

FIG. 15 illustrates accuracy and applicability of the method for magnetic nanoparticle temperature imaging when the DC gradient magnetic field is nonlinear. It can be inferred that temperature measurement error is less than 0.54K under an SNR of 80 dB, which shows that the method features comparatively high accuracy of temperature measurement and has some anti-noise performance when the DC gradient magnetic field is nonlinear.

As a result, accuracy, stability and reproducibility of the method for magnetic nanoparticle temperature imaging are guaranteed, which provides a reliable method for accurate, rapid and noninvasive temperature field imaging of a living body under complicated circumstances.

While preferred embodiments of the invention have been described above, the invention is not limited to disclosure in the embodiments and the accompanying drawings. Any changes or modifications without departing from the spirit of the invention fall within the scope of the invention.

What is claimed is:

1. A method for magnetic nanoparticle temperature imaging, comprising steps of:
   (1) positioning magnetic nanoparticles at a one-dimensional space of interest;
   (2.1) applying a DC magnetic field $H_{dc}=b$ and an AC excited magnetic field simultaneously to the one-dimensional space, and
   (2.2) collecting a first AC magnetization signal of the magnetic nanoparticles via a data acquisition card, thereby obtaining amplitudes $A_1, A_3 \ldots A_{2j-1}$ of odd harmonics of the first AC magnetization signal, where a number of harmonics $j \geq 2$, and b is amplitude of the DC magnetic field;
   (3.1) substituting a combined DC magnetic field $$H'_{dc} = \begin{cases} b & x < x_1 \\ f(x) & x_1 \leq x \leq x_1 + \Delta x \\ -b & x > x_1 + \Delta x \end{cases}$$

for the DC magnetic field in step (2.1) while keeping the AC excited magnetic field in step (2.1) unchanged, where x represents position, $x_1$ is starting position of a DC gradient magnetic field $f(x)$ in the one-dimensional space, and $\Delta x$ is width of the DC gradient magnetic field $f(x)$, and
   (3.2) collecting a second AC magnetization signal of the magnetic nanoparticles via the data acquisition card, thereby obtaining amplitudes $B_1, B_3 \ldots B_{2j-1}$ of odd harmonics of the second AC magnetization signal;
   (4) calculating variations $S_1, S_3 \ldots S_{2j-1}$ between the amplitudes $B_1, B_3 \ldots B_{2j-1}$ of step (3.2) and the amplitudes $A_1, A_3 \ldots A_{2j-1}$ of step (2.2);
   (5) calculating parameter y of an area of $[x_1, x_1+\Delta x]$ according to equations between the variations and in-vivo temperature $$S_1 = \sum_{k=1}^{m} c \cdot f_1(y, z(r_k)) - \sum_{k=1}^{m} c \cdot f_1(y, z)\bigg|_{z=b}$$

$$S_3 = \sum_{k=1}^{m} c \cdot f_3(y, z(r_k)) - \sum_{k=1}^{m} c \cdot f_3(y, z)\bigg|_{z=b}$$

$$\vdots$$

-continued $$S_{2j-1} = \sum_{k=1}^{m} c \cdot f_{2j-1}(y, z(r_k)) - \sum_{k=1}^{m} c \cdot f_{2j-1}(y, z)\bigg|_{z=b}$$

thereby obtaining in-vivo temperature $$T = \frac{M_s}{k_0 \cdot y}$$

of the area of $[x_1, x_1+\Delta x]$, where $c=NM_S$, N is concentration of the magnetic nanoparticles, $M_s$ is effective atomic magnetic moment of the magnetic nanoparticles, $k_0$ is Boltzmann's constant, magnetization of the magnetic nanoparticles is described by Langevin's function, $c \cdot f_{2j-1}(y,z(r_k))$ is an amplitude of a $(2j-1)^{th}$ harmonic obtained by finite terms of Taylor series expansion of the Langevin's function, $z(r_k)$ is intensity of the DC magnetic field at a $k^{th}$ discrete point $r_k$ in the area of $[x_1, x_1+\Delta x]$, and m is a number of discrete points in the area of $[x_1, x_1+\Delta x]$, and
   (6.1) changing the starting position of the DC gradient magnetic field $f(x)$ relative to the one-dimensional space so that the DC gradient magnetic field $f(x)$ with the width of $\Delta x$ moves to a next area,
   (6.2) repeating steps (3.1)~(5) thereby obtaining in-vivo temperature of the next area until temperature measurement of the whole one-dimensional space is completed.

2. The method of claim 1, wherein step (6.1) is performed by moving a DC magnetic field generating device or by changing current of an exciting coil.

3. The method of claim 1, wherein steps (2.2) and (3.2) are performed by a digital phase-sensitive detection method or by a least squares system parameter identification method.

4. The method of claim 1, wherein the DC gradient field is generated by one or more exciting coils.

5. The method of claim 4, wherein step (6.1) is performed by changing the relative position between the one-dimensional space and the one or more exciting coils via a motor or by changing current of the one or more exciting coils.

6. The method of claim 1 further comprising
   (6.3) generating an image reflective of a plurality of positions in the one-dimensional space and corresponding temperature measurement at each of the plurality of positions.

7. A system for magnetic nanoparticle temperature imaging, comprising:
   a DC magnetic field generating device, operable for applying a DC magnetic field $H_{dc}=b$ to a one-dimensional space where magnetic nanoparticles are positioned, where b is amplitude of the DC magnetic field;
   a combined DC magnetic field generating device, operable for applying a combined DC magnetic field $$H'_{dc} = \begin{cases} b & x < x_1 \\ f(x) & x_1 \leq x \leq x_1 + \Delta x \\ -b & x > x_1 + \Delta x \end{cases}$$

to the one-dimensional space, where x represents position, $x_1$ is starting position of a DC gradient magnetic field $f(x)$ in the one-dimensional space, and $\Delta x$ is width of the DC gradient magnetic field $f(x)$;

an AC excited magnetic field generating device, operable for applying an AC excited magnetic field to the one-dimensional space;

a magnetization collecting device, operable for collecting AC magnetization signals of the magnetic nanoparticles positioned at the one-dimensional space; wherein the magnetization collecting device is a data acquisition card; and a processor, operable for processing a first AC magnetization signal collected by applying the DC magnetic field and the AC excited magnetic field simultaneously to the magnetic nanoparticles thereby obtaining amplitudes $A_1, A_3 \ldots A_{2j-1}$ of odd harmonics of the first AC magnetization signal, processing a second AC magnetization signal collected by applying the combined DC magnetic field and the AC excited magnetic field simultaneously to the magnetic nanoparticles thereby obtaining amplitudes $B_1, B_3 \ldots B_{2j-1}$ of odd harmonics of the second AC magnetization signal, calculating variations $S_1, S_3 \ldots S_{2j-1}$ between the amplitudes $B_1, B_3 \ldots B_{2j-1}$ and the amplitudes $A_1, A_3 \ldots A_{2j-1}$, and calculating parameter y of an area of $[x_1, x_1+\Delta x]$ according to equations between the variations and in vivo temperature $$S_1 = \sum_{k=1}^{m} c \cdot f_1(y, z(r_k)) - \sum_{k=1}^{m} c \cdot f_1(y, z)\bigg|_{z=b}$$

$$S_3 = \sum_{k=1}^{m} c \cdot f_3(y, z(r_k)) - \sum_{k=1}^{m} c \cdot f_3(y, z)\bigg|_{z=b}$$

$$\vdots$$

$$S_{2j-1} = \sum_{k=1}^{m} c \cdot f_{2j-1}(y, z(r_k)) - \sum_{k=1}^{m} c \cdot f_{2j-1}(y, z)\bigg|_{z=b}$$

thereby obtaining in-vivo temperature $$T = \frac{M_s}{k_0 \cdot y}$$

of the area of $[x_1, x_1+\Delta x]$, where $c=NM_s$, N is concentration of the magnetic nanoparticles, $M_s$ is effective atomic magnetic moment of the magnetic nanoparticles, $k_0$ is Boltzmann's constant, magnetization of the magnetic nanoparticles is described by Langevin's function, $c \cdot f_{2j-1}(y, z(r_k))$ is amplitude of a $(2j-1)^{th}$ harmonic obtained by finite terms of Taylor series expansion of the Langevin's function, $z(r_k)$ is intensity of the DC magnetic field at a $k^{th}$ discrete point $r_k$ in the area of $[x_1, x_1+\Delta x]$, m is a number of discrete points in the area of $[x_1, x_1+\Delta x]$, and a number of the harmonics $j \geq 2$.

8. The system of claim 7, further comprising a scanning device, operable for moving the relative position between the one-dimensional space and the combined DC magnetic field generating device.

9. The system of claim 8, wherein the mechanical scanning device comprises a motor.

10. A method for magnetic nanoparticle temperature imaging, comprising steps of:
(1) positioning magnetic nanoparticles at a one-dimensional space of interest;

(2.1) applying a DC magnetic field $H_{dc}=b$ and an AC excited magnetic field simultaneously to the one-dimensional space, and (2.2) collecting a first AC magnetization signal of the magnetic nanoparticles via a data acquisition card, thereby obtaining amplitudes $A_1, A_3 \ldots A_{2j-1}$ of odd harmonics of the first AC magnetization signal, where a number of harmonics $j \geq 2$, and b is amplitude of the DC magnetic field;

(3.1) substituting a combined DC magnetic field $$H'_{dc} = \begin{cases} b & x < x_1 \\ f(x) & x_1 \leq x \leq x_1 + \Delta x \\ -b & x > x_1 + \Delta x \end{cases}$$

for the DC magnetic field in step (2.1) while keeping the AC excited magnetic field in step (2.1) unchanged, where x represents position, $x_1$ is starting position of a DC gradient magnetic field f(x) in the one-dimensional space, and $\Delta x$ is width of the DC gradient magnetic field f(x), wherein the DC gradient field is generated by one or more exciting coils; and (3.2) collecting a second AC magnetization signal of the magnetic nanoparticles via the data acquisition card, thereby obtaining amplitudes $B_1, B_3 \ldots B_{2j-1}$ of odd harmonics of the second AC magnetization signal;

(4) calculating variations $S_1, S_3 \ldots S_{2j-1}$ between the amplitudes $B_1, B_3 \ldots B_{2j-1}$ of step (3.2) and the amplitudes $A_1, A_3 \ldots A_{2j-1}$ of step (2.2);

(5) calculating parameter y of an area of $[x_1, x_1+\Delta x]$ according to equations between the variations and in-vivo temperature $$S_1 = \sum_{k=1}^{m} c \cdot f_1(y, z(r_k)) - \sum_{k=1}^{m} c \cdot f_1(y, z)\bigg|_{z=b}$$

$$S_3 = \sum_{k=1}^{m} c \cdot f_3(y, z(r_k)) - \sum_{k=1}^{m} c \cdot f_3(y, z)\bigg|_{z=b}$$

$$\vdots$$

$$S_{2j-1} = \sum_{k=1}^{m} c \cdot f_{2j-1}(y, z(r_k)) - \sum_{k=1}^{m} c \cdot f_{2j-1}(y, z)\bigg|_{z=b}$$

thereby obtaining in-vivo temperature $$T = \frac{M_s}{k_0 \cdot y}$$

of the area of $[x_1, x_1+\Delta x]$, where $c=NM_s$, N is concentration of the magnetic nanoparticles, $M_s$ is effective atomic magnetic moment of the magnetic nanoparticles, $k_0$ is Boltzmann's constant, magnetization of the magnetic nanoparticles is described by Langevin's function, $c \cdot f_{2j-1}(y, z(r_k))$ is an amplitude of a $(2j-1)^{th}$ harmonic obtained by finite terms of Taylor series expansion of the Langevin's function, $z(r_k)$ is intensity of the DC magnetic field at a $k^{th}$ discrete point $r_k$ in the area of $[x_1, x_1+\Delta x]$, and m is a number of discrete points in the area of $[x_1, x_1+\Delta x]$; and (6.1) changing the starting position of the DC gradient magnetic field f(x) relative to the one-dimensional space via a motor or by changing current of the one or more exciting coils, so that the DC gradient magnetic field f(x) with the width of Δx moves to a next area, (6.2) repeating steps (3.1)~(5) thereby obtaining in-vivo temperature of the next area until temperature measurement of the whole one-dimensional space is completed, (6.3) generating an image reflective of a plurality of positions in the one-dimensional space and corresponding temperature measurement at each of the plurality of positions.

\* \* \* \* \*